United States Patent
Bonauer et al.

(10) Patent No.: US 9,339,666 B2
(45) Date of Patent: *May 17, 2016

(54) HAIR COLOURING METHODS AND KITS THEREOF

(71) Applicant: The Procter & Gamble Company, Cincinnati, OH (US)

(72) Inventors: Christoph Hans Peter Bonauer, Frankfurt (DE); Gabriele de Waal, Grob-Umstadt (DE); Graham John Myatt, Cincinnati, OH (US); Stephen Robert Schofield, London (GB); Nan Wang, Frankfurt (DE); Jennifer Mary Marsh, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/465,434

(22) Filed: Aug. 21, 2014

(65) Prior Publication Data

US 2015/0053231 A1 Feb. 26, 2015

Related U.S. Application Data

(60) Provisional application No. 61/869,201, filed on Aug. 23, 2013.

(51) Int. Cl.
| | |
|---|---|
| *A61Q 5/10* | (2006.01) |
| *A45D 19/00* | (2006.01) |
| *A61K 8/22* | (2006.01) |
| *A61K 8/92* | (2006.01) |
| *A61K 8/34* | (2006.01) |
| *A61K 8/891* | (2006.01) |
| *A61K 8/91* | (2006.01) |

(52) U.S. Cl.
CPC ............. *A61Q 5/10* (2013.01); *A45D 19/0008* (2013.01); *A61K 8/22* (2013.01); *A61K 8/345* (2013.01); *A61K 8/891* (2013.01); *A61K 8/91* (2013.01); *A61K 8/92* (2013.01); *A45D 2019/0066* (2013.01); *A61K 2800/43* (2013.01); *A61K 2800/432* (2013.01); *A61K 2800/882* (2013.01)

(58) Field of Classification Search
CPC ............. A61Q 5/10; A61K 8/22; A61K 8/92; A61K 2800/882; A45D 2019/0066; A45D 19/0008
USPC ........................................ 8/405; 132/202, 208
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 6,099,828 A | 8/2000 | Kajino | |
| 6,835,018 B2 | 12/2004 | Miczewski | |
| 7,875,269 B2 | 1/2011 | Bureiko | |
| 8,632,611 B2 * | 1/2014 | Agostino | ............... A61K 8/731 132/202 |
| 2008/0178399 A1 * | 7/2008 | Vena | ...................... A61K 8/463 8/407 |

FOREIGN PATENT DOCUMENTS

| | | |
|---|---|---|
| FR | 2953397 B1 | 1/2012 |
| JP | 08333224 A | 12/1996 |
| JP | 2010248103 A | 11/2010 |

* cited by examiner

*Primary Examiner* — Eisa Elhilo
(74) *Attorney, Agent, or Firm* — James T. Fondriest

(57) ABSTRACT

Method for coloring hair wherein a non-diluted hair coloring composition is applied to the hair, e.g. the hair roots and a diluted hair coloring composition is applied to the hair, e.g. the hair lengths and tips, wherein a dilutant composition comprising a non-aqueous liquid is added to the non-diluted hair coloring composition to obtain the diluted hair coloring composition.

18 Claims, No Drawings

HAIR COLOURING METHODS AND KITS THEREOF

FIELD OF THE INVENTION

The invention relates to a method of hair colouring and kits thereof.

BACKGROUND OF THE INVENTION

Consumers desiring to colour their hair typically have two options available namely to use a commercially available retail product or kit or use the services of a professional salon. The latter whilst providing a highly desirable colour outcome, is considerably more expensive than the retail option and thus not available to many consumers particularly those who colour regularly.

For consumers who have previously coloured their hair, the colour and condition of the hair is not homogenous along the entire length. The hair strands will comprise root virgin hair or new growth hair which has not been previously coloured and conversely at the tips hair which has experienced one or multiple hair colouring treatments. The tips of the hair are typically the most damaged portions of the hair and are characterised by an overly deposition of dyes or over-bleaching due to previous oxidative hair colorations. The intermediate hair length is typically a medium between these two extreme conditions. However, the problem with current retail hair colour products is that they do not take into account the differences of properties between the different portions of the hair. It is rather challenging even for experienced home colour users to control the dye deposition or the bleaching provided by a retail hair colour product in order to not overly deposit hair dyes on or over-bleaching hair lengths and tips since the instructions provided in hair colour retail kits are typically imprecise, often not followed and the results achieved are not comparable with those from a salon stylist. The overall colour appearance is typically not as homogeneous as that provided by a salon stylist.

Therefore, there is a need to provide a simple method as well as a simple retail kit for colouring or bleaching hair which gives the user the possibility of obtaining a different hair colour or bleaching effect on different portions of the hair, for example a different colour effect on hair roots vs. hair lengths and tips to provide a smooth root-to-tip transition on hair which has been previously coloured.

SUMMARY OF THE INVENTION

The present invention relates to a method for colouring hair comprising the steps of:
i) mixing a developer composition with a dye composition to obtain a non-diluted hair colouring composition, wherein the developer composition comprises one or more oxidizing agents and the dye composition comprises one or more oxidative dye precursors and/or one or more alkalising agents;
ii) applying a first portion of the non-diluted hair colouring composition obtained in step i) to the hair and retaining a second portion of the non-diluted hair colouring composition obtained in step i);
iii) mixing the second portion with a dilutant composition comprising a non-aqueous liquid to obtain a diluted hair colouring composition;
iv) applying a portion or all of the diluted hair colouring composition to the hair;

The present invention also relates to a hair colouring kit comprising a developer composition comprising one or more oxidizing agents, a dye composition comprising one or more oxidative dye precursors and/or one or more alkalising agents and a dilutant composition comprising a non-aqueous liquid.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention. The terms "root", "hair roots", "root hair line" and "virgin hair" all refer to hair which has not been previously treated with a hair colouring or bleaching composition.

By "hair colouring" composition it is meant a composition suitable for changing the color of hair. The hair colouring composition can comprise oxidative dye precursors, direct dyes or even no, or substantially no, dyes in case of bleaching only compositions where the change of colour is mainly caused by the degradation of the natural melanin contained in the hair shaft by the oxidizing agent. The terms "hair colouring composition" and "method for colouring hair" as used herein also encompasses respectively the terms "hair bleaching composition" and "method for bleaching hair".

In the preferred embodiment according to the present invention, the hair colouring compositions are applied to hair which has already been previously coloured with hair colouring compositions. In such a case, the terms "root", "hair roots", "root hair line" and "virgin hair" all refer to the portion of hair having grown, since the last hair colouration, said portion of hair being virgin, i.e. naturally-coloured and the terms "hair lengths and tips" refer to the remaining portion of hair having been already previously coloured.

By "liquid" it is meant liquid at 25° C. and at atmospheric pressure (760 mmHg).

By "water-miscible liquid" it is meant a liquid which has a miscibility with water of 50% by weight or more at 25° C. and at atmospheric pressure (760 mmHg).

By "water-immiscible liquid" it is meant a liquid which has a miscibility with water of less than 50% by weight at 25° C. and at atmospheric pressure (760 mmHg).

By "dilutant composition" it is meant diluent composition.

By "oil" it is meant an organic compound that is insoluble in water at ordinary temperature (25° C.) and at atmospheric pressure (760 mmHg), i.e. it has a water solubility of less than 5% by weight, preferably less than 1% by weight, even more preferably less than 0.1% by weight. Oils have in their structure at least one hydrocarbon-based chain comprising at least six carbon atoms or a sequence of at least two siloxane groups. In addition, oils are soluble in organic solvents under the same temperature and pressure conditions, for instance chloroform, ethanol or benzene. Furthermore, oils are liquid at ordinary temperature (25° C.) and at atmospheric pressure (760 mmHg).

All percentages are by weight of the total composition unless specifically stated otherwise. All ratios are weight ratios unless specifically stated otherwise.

Method for Colouring Hair

The present invention relates to a method for colouring hair as stated hereinbefore.

The method may further comprise the step v) of rinsing the hair.

The non-diluted hair colouring composition may be applied to the hair roots and the diluted hair colouring composition may be applied to the hair lengths and tips.

Natural hair typically goes from darker to lighter when moving from the roots to the tips. The inventors have surprisingly found that by carrying out a method for colouring hair according to the present invention it is possible to preserve a more natural root-to-tip transition. In addition, the hair is not a flat block color, but shows more of the natural variation of tones in the hair as a diluted colorant is applied to the lengths. Whilst not being bound by theory it is believed that mixing the developer composition with the dye composition to obtain a non-diluted composition and applying a first portion of the non-diluted composition directly onto the root virgin hair, delivers an effective composition to both lighten and colour previously uncoloured hair to the desired level. However, retaining a second portion of this non-diluted composition and mixing it with a dilutant composition thereto provides a resultant diluted composition which reduces the overall effective lightening and colouring capacity of the non-diluted composition which can then be applied to the remaining pre-coloured hair length which requires less lightening and dye deposition in order to deliver a colour result similar to that resulting from the application of the first portion of the non-diluted composition applied to the roots.

The non-aqueous liquid comprised in the dilutant composition may be a water-miscible liquid or a water-immiscible liquid.

The water-miscible liquid may be selected from alcohols, ethers, esters, and mixtures thereof. The water-miscible liquid may be selected from C1 to C4 lower alkanols (such as ethanol, propanol, isopropanol, butanol and mixtures thereof), aromatic alcohols (such as benzyl alcohol and/or phenoxyethanol), polyols and polyol ethers (such as 2-butoxyethanol, propylene glycol, propylene glycol monomethyl ether, diethylene glycol monoethyl ether, hexylene glycol, glycerin, ethoxy diglycol, butoxydiglycol, dipropylene glycol, polyglycerol, sorbitol, polyethylene glycol, polypropylene glycol, and mixtures thereof), propylene carbonate, ethylene glycol distearate (EGDS) and mixtures thereof. The water-miscible liquid may be selected from ethanol, propanol, isopropanol, glycerin, propylene glycol, hexylene glycol, ethoxydiglycol, and mixtures thereof. Whilst not wishing to be bound by theory, it is believed that mixing the second portion of the non-diluted composition with a dilutant composition comprising a non-aqueous liquid which is water-miscible may reduce the concentration of actives species such as dye precursors, oxidizing agent such as hydrogen peroxide and alkalising agents in the composition which may lead to a reduction in both reaction kinetics of dye formation and penetration of actives into hair.

The water-immiscible liquid may be an oil. The oil may be selected from fatty acids, lower alkanes, fatty alcohols, esters of fatty acid, esters of fatty alcohol, oils such as mineral, vegetable, animal and synthetic non-silicone oils, non-silicone waxes, silicones and mixtures thereof. Lower alkanes have from 6 to 16 carbon atoms and are linear or branched, optionally cyclic. As examples, alkanes can be chosen from hexane and dodecane, isoparaffins such as isohexadecane and isodecane. Whilst not wishing to be bound by theory, it is believed that by mixing the second portion of the non-diluted composition with a dilutant composition comprising a non-aqueous liquid which is water-immiscible, some of the dye precursors may partition into the non-water phase of the composition which may lead to a reduction of their ability to diffuse into the hair and to take part in dyeing reactions.

The dilutant composition may comprise water, for example less than 75%, or less than 25% of water. This may be the case when the non-aqueous liquid comprised in the dilutant composition is water-miscible liquid.

In step iii) of the method, the second portion of the non-diluted hair colouring composition obtained in step i) may be mixed with the dilutant composition at a mixing ratio of 30:1 or less or 4:1 or less. The mixing ratio may be from 1:2 to 30:1, or from 1:2 to 4:1, or from 1:2 to 2:1 or of 2:1, Alternatively, the mixing ratio may be of less than 1:2, or from 1:25 to 1:2.1, or from 1:20 to 1:2.1, or from 1:10 to 1:2.1 or from 1:5 to 1:2.1.

In step i) of the method, the developer composition may be mixed with the dye composition at a mixing ratio of 1:3 to 2:1, or 1:2 to 2:1 or 1:1.

In step ii) of the method, from 90% to 10%, or from 80% to 50%, or from 75% to 55%, or from 75% to 60% by weight of the non-diluted hair colouring composition may be applied as a first portion to the hair, preferably the hair roots.

In some embodiments, the method may further comprise the step of waiting for a time period of from 10 min to 40 min, or from 15 min to 30 min or from 20 min, which is performed between steps ii) and iv) and the step of waiting for a time period of from 5 min to 20 min or 10 min which is performed between steps iv) and v).

Alternatively, in some embodiments, step iii) may be performed immediately after step ii) and step iv) may be performed immediately after step iii) and the method further comprises the step of waiting for a time period of from 5 min to 40 min, or from 20 min to 40 min, or of 30 min, which is performed between steps iv) and v). The inventors have surprisingly found that these embodiments may be used for colouring hair with non-tonal shades such as blonde, brown or black hair shades in case the second portion of the non-diluted hair colouring composition obtained in step i) is mixed with the dilutant composition at a mixing ratio of less than 1:2 or from 1:25 to 1:2.1, or from 1:20 to 1:2.1, or from 1:10 to 1:2.1 or from 1:5 to 1:2.1. This is a simpler application process for the user who doesn't need to wait and time itself. This leads to a more consistent colour result as we are reducing any variability from users having to follow and comply with instructions.

The developer composition may comprise from 1% to 20% by weight of the oxidizing agents and/or the dye composition may comprise from 0.01% to 10% by weight of the oxidative dye precursors and/or from 0.1% to 10% by weight of the alkalising agents.

The dilutant composition may comprise any ingredient which is typically comprised in hair colouring compositions. The dilutant composition may comprise one or more active components selected from surfactants, conditioning agents, polymers, and mixtures thereof.

The dilutant composition may comprise these active components at a level of up to 25% by weight of the dilutant composition.

The volume of the developer composition may be from 10 mL to 120 mL, or from 40 mL to 70 mL, or from 55 mL to 65 mL. The volume of the dye composition used in step i) of the method may be from 10 mL to 120 mL, or from 40 mL to 70 mL, or from 55 mL to 65 mL. The volume of dilutant composition may be from 10 mL to 70 mL, or from 15 mL to 30 mL, or from 20 mL to 25 mL.

The present description is not limited to the embodiments wherein only two different hair colouring compositions, namely a non-diluted and a diluted hair colouring compositions are applied to the hair. It may be envisaged to apply more than two different hair colouring compositions to the hair wherein each time the next composition is further diluted with the addition of a dilutant composition comprising a non-aqueous liquid.

Hair Colouring Compositions

Other Ingredients

The non-diluted and/or diluted hair colouring compositions of the present invention may comprise, in addition to the ingredients indicated above, further ingredients in order to further enhance the properties of the compositions, as long as these are not excluded by the claims.

Suitable further ingredients include, but not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The non-diluted and/or the diluted hair colouring compositions according to the present invention may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as 2-butoxyethanol, propylene glycol, propylene glycol monomethyl ether, diethylene glycol monoethyl ether, hexylene glycol, glycerol, ethoxydiglycol, butoxydiglycol, dipropylene glycol, polyglycerol), propylene carbonate and mixtures thereof.

The solvent may be selected from the group consisting of water, ethanol, propanol, isopropanol, glycerol, propylene glycol, hexylene glycol, ethoxydiglycol, and mixtures thereof.

Typically, the non-diluted and/or the diluted hair colouring compositions may comprise water as a main ingredient, particularly in a total amount ranging from at least 50%, alternatively from at least 60%, alternatively from at least 70%, by weight of the total composition. Typically, when present, the non-diluted and/or the diluted hair colouring compositions may comprise a total amount of organic solvents ranging from 1% to 30%, by weight of the total composition.

Oxidizing Agents

The non-diluted and/or the diluted hair colouring compositions according to the present invention may further comprise at least one source of an oxidizing agent. Any oxidizing agent known in the art may be used. Preferred oxidizing agents are water-soluble peroxygen oxidizing agents. As used herein, "water-soluble" means that in standard conditions at least 0.1 g, preferably 1 g, more preferably 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

Typically, the non-diluted and/or the diluted hair colouring compositions may comprise a total amount of oxidizing agents ranging from 0.1% to 10%, alternatively from 1% to 7%, alternatively from 2% to 5%, by weight of the total composition.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

The non-diluted and/or the diluted hair colouring compositions may comprise a water-soluble oxidizing agent selected from the group consisting of hydrogen peroxide, percarbonates (which may be used to provide a source of both oxidizing agent and carbonate ions and or ammonium ions), persulphates, and mixtures thereof.

When the non-diluted and/or the diluted hair colouring compositions of the present invention are obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise 6% or 9% of the $H_2O_2$ relative to the total weight of the developer composition. A commercial example is the Welloxon® Emulsion with respectively 6% and 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

Alkalizing Agents

The non-diluted and/or the diluted hair colouring compositions according to the present invention may further comprise one or more alkalizing agents. Any alkalizing agent known in the art may be used.

Typically, the non-diluted and/or the diluted hair colouring compositions may comprise a total amount of alkalizing agents ranging from 0.1% to 10%, alternatively from 0.5% to 6%, alternatively from 1% to 4%, by weight of the total composition.

Suitable alkalizing agents include, but are not limited to ammonia; alkanolamines (such as monoethanolamine, diethanolamine, triethanolamine, monopropanolamine, dipropanolamine, tripropanolamine); 2-amino-2-methyl-1, 3-propanediol, 2-amino-2-methyl-1-propanol, and 2-amino-2-hydroxymethyl-1,3-propanediol; guanidium salts; alkali metal and ammonium hydroxides (such as sodium hydroxide); alkali metal and ammonium carbonates; and mixtures thereof. Typical alkalizing agents are ammonia and/or monoethanolamine. Preferably, if present, the ammonium ions and carbonate ions are present in the composition at a weight ratio of from 3:1 to 1:10, alternatively from 2:1 to 1:5.

When the non-diluted and/or the diluted hair colouring compositions of the present invention are obtained by mixing a developer composition and a dye composition prior to use, the alkalizing agent is generally present in the dye composition.

Oxidative Dye Precursors

The non-diluted and/or the diluted hair colouring compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the non-diluted and/or the diluted hair colouring compositions may comprise a total amount of oxidative dye precursors ranging up to 12%, alternatively from 0.1% to 10%, alternatively from 0.3% to 8%, alternatively from 0.5% to 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the non-diluted and/or diluted hair colouring compositions of the invention are obtained by mixing a dye composition and a developer composition, the primary intermediates and couplers are usually incorporated into the dye composition.

Direct Dyes

The non-diluted and/or the diluted hair colouring compositions according to the present invention may further comprise compatible direct dyes, in an amount sufficient to provide additional coloring, particularly with regard to intensity. Typically, the compositions may comprise a total amount of direct dyes ranging from 0.05% to 4%, by weight of the total composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the non-diluted and/or the diluted hair colouring compositions are obtained by mixing a dye composition and a developer composition, the direct dyes are usually incorporated into the dye composition.

Chelants

The non-diluted and/or the diluted hair colouring compositions according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the non-diluted and/or the diluted compositions may comprise a total amount of chelants ranging from at least 0.01%, alternatively from 0.01% to 5%, alternatively from 0.25% to 3%, alternatively from 0.5% to 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalyldi(sulfosuccinic acids) (DDS), N,N'-bis(2-hydroxybenzyl) ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, (3-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative —$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the non-diluted and/or the diluted hair colouring compositions comprise a chelant selected from the group consisting of diethylenetriamine-N, N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the non-diluted and/or the diluted hair colouring compositions of the invention are obtained by mixing a dye composition and a developer composition, the chelants may be incorporated in the dye composition and/or in the developer composition. A chelant is usually present in the developer composition for stability reason.

Radical Scavengers

The non-diluted and/or the diluted hair colouring compositions according to the present invention may further comprise a radical scavenger. As used herein the term "radical scavenger" refers to a species that can react with a radical, preferably a carbonate radical to convert the radical species by a series of fast reactions to a less reactive species. The radical scavenger may be different from the alkalizing agent and/or is present in an amount sufficient to reduce the damage to the hair during the colouring/bleaching process.

Typically, the non-diluted and/or the diluted hair colouring compositions may comprise a total amount of radical scavengers ranging from 0.1% to 10%, alternatively from 1% by weight to 7%, by weight of the total composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifier and Buffering Agents

The non-diluted and/or the diluted hair colouring compositions according to the present invention may further comprise, in addition to the alkalizing agent discussed above, a pH modifier and/or buffering agent in an amount that is sufficiently effective to adjust the pH of the composition to fall within a range from 3 to 13, alternatively from 8 to 12, alternatively from 9 to 11.

Suitable pH modifiers and/or buffering agents include, but are not limited to: ammonia; alkanolamines (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifier and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The non-diluted and/or the diluted hair colouring compositions according to the invention may further comprise a thickener in an amount sufficient to provide the composition with a viscosity so that it can be readily applied to the hair without unduly dripping off the hair and causing mess.

Typically, the non-diluted and/or the diluted hair colouring compositions may comprise a total amount of thickeners ranging from at least 0.1%, alternatively at least 0.5%, alternatively at least 1%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below

$$CH2=C(R1)CH2OBnR \qquad (I)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (II) below

$$CH2=C(R1)COOH \qquad (II)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (III) below

$$CH2=C(R1)COOBnR2 \qquad (III)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (IV) below

$$CH2=C< \qquad (IV)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch. Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrrolidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Di-cetyl phosphate and Cetearyl alcohol (available as Crodafos CES), and mixtures thereof.

Thickeners for use in the developer composition may include acrylates copolymer, hydrophobically modified acrylate copolymers (e.g. Acrylates/Steareth-20 Methacrylate Copolymer) and mixtures thereof. Thickeners for use in the dye composition may include blends of Ceteth—10 phosphate, Di-cetyl phosphate and Cetearyl alcohol (as CRODAFOS CES).

Gel Network Thickener System

The non-diluted and/or diluted hair colouring compositions of the present invention may comprise at at least one gel network thickener system. Said system may comprise at least one low HLB surfactant and/or amphophile having a high melting point, and at least one additional second surfactant as specified hereinafter. Suitable gel network thickener systems are disclosed in PCT application WO2006/060598A1.

Said low HLB surfactant and/or amphophile may have preferably an HLB of 6 or less and melting point of at least 30° C. It may be selected from the group consisting of cetyl, stearyl, cetostearyl or behenyl alcohols, steareth-2, glycerol monostearate and mixtures thereof. Said second surfactant may be anionic, non-ionic or cationic. Anionic surfactants may be selected from the group consisting of alkyl ether phosphates having in average 1-3 ethylene oxide units and comprising an alkyl radical comprising from 8 to 30 carbon atoms. Said non-ionic surfactants may be selected from the group consisting of those comprising one or more polyethyleneoxide chain including polyoxyethylene alkyl ethers having from 100 to 200 ethylene oxide units (e.g. steareth-100, steareth-150). Said cationic surfactant may be selected from the group consisting of behentrimonium chloride, behenamidopropyltrimonium methosulfate, stearamidopropyltrimonium chloride, arachidtrimonium chloride and mixtures thereof. A preferred gel network thickening system comprises fatty alcohols having 14 to 30 carbon atoms (cetyl and/or stearyl alcohol) and alkyl ether phosphates (e.g. from 1 to 3 ethylene oxide units). The non-diluted and/or diluted hair colouring compositions of the present invention may comprise a total amount of gel network thickening system of from 2% to 10% by weight of respectively the non-diluted and/or diluted hair colouring composition. The weight ratio of the low HLB surfactants to the second specified surfactants is preferably from 10:1 to 1:1.

Carbonate Ion Sources

The non-diluted and/or the diluted hair colouring compositions according to the present invention may further comprise a source of carbonate ions, carbamate ions, hydrogen carbonate ions, and mixtures thereof in a sufficient amount to reduce damage to the hair during the coloring process. Typically, the non-diluted and/or the diluted hair colouring compositions may comprise a total amount of a carbonate ion source ranging from 0.1% to 15%, alternatively from 0.1% to 10%, alternatively from 1% to 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The non-diluted and/or the diluted hair colouring compositions according to the present invention may further comprise a conditioning agent, and/or be used in combination with a composition comprising a conditioning agent.

Typically, the non-diluted and/or the diluted hair colouring compositions may comprise a total amount of conditioning agents ranging from 0.05% to 20%, alternatively from 0.1% to 15%, alternatively from 0.2% to 10%, alternatively from 0.2% to 2%, alternatively from 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane ($Si(CH_3)_2$—O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si$—O, $R_{12}(CH_3)_2Si$—O, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from 500 to $5 \times 10^6$, alternatively from 1000 to $3 \times 10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinylpyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); copolymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum C W, Kiprogum N G K by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)-A1-N+(R3)(R4)-B1-] [2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

The cationic polymer may be selected from the group consisting of polyquaternium 37, polyquaternium 7, polyquaternium 22, polyquaternium 87, and mixtures thereof; particularly from the group consisting of polyquaternium 37, polyquaternium 22, and mixtures thereof.

Surfactants

The non-diluted and/or the diluted hair colouring compositions according to the present invention may further comprise a surfactant. Suitable surfactants generally have a lipophilic chain length of from 8 to 30 carbon atoms and can be selected from anionic surfactants, nonionic surfactants, amphoteric surfactants, cationic surfactants, and mixtures thereof.

Typically, the non-diluted and/or the diluted hair colouring compositions may comprise a total amount of surfactants ranging from 1% to 60%, alternatively from 2% to 30%, alternatively from 8% to 25%, alternatively from 10% to 20%, by weight of the total composition.

The non-diluted and/or the diluted hair colouring compositions may comprise a mixture of an anionic surfactant and an amphoteric surfactant with one or more nonionic surfactants. The compositions may comprise a total amount of anionic surfactant ranging from 0.1% to 20%, alternatively from 0.1% to 15%, alternatively from 5% to 15%, by weight of the total composition; and a total amount of amphoteric and/or nonionic components, which may range independently from each other from 0.1% to 15%, alternatively from 0.5% to 10%, alternatively from 1% to 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CONHCH$_2$CH$_2$—N$^+$($R_3$)($R_4$)(CH$_2$COO$^-$), (VI) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (VII) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (VIII) below:

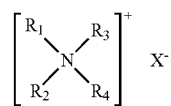

(VIII)

wherein X$^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from ($C_{12}$-$C_{22}$)alkylamido($C_2$-$C_6$)alkyl and ($C_{12}$-$C_{22}$) alkylacetate radicals. A suitable cationic surfactant is, for example, a dicetyldimethyl ammonium salt (for example chloride);

B) Quaternary ammonium salts of imidazolinium of formula (IX) below:

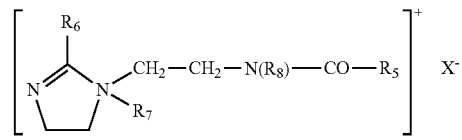

(IX)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and X$^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (X):

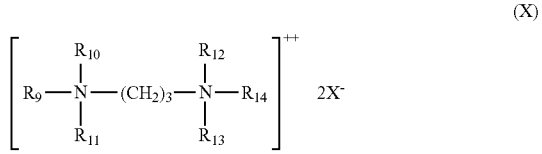

in which $R_9$ is chosen from aliphatic radicals comprising from 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XI) below:

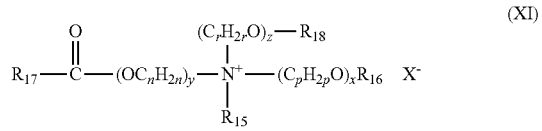

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XI) can be used, in which: R15 is chosen from methyl and ethyl radicals, x and y are equal to 1; z is equal to 0 or 1; n, p and r are equal to 2; R16 is chosen from: a radical R19C(O)—,methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Ionic Strength

The non-diluted and/or the diluted hair colouring compositions of the present invention may further have an ionic strength as defined herein of less than 1.35 mole/kg, alternatively from 0.10 to 0.75 mole/kg, alternatively from 0.20 to 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the composition is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: I=½((2×(+1)²×0.050)+(+1)²×0.020+(-2)²×0.050+(-1)²×0.020)=0.17 M.

Foam

The non-diluted and/or the diluted hair colouring compositions of the invention may be provided in the form of foam which is applied to the hair. Foam formation is typically achieved by the use of a foaming agent incorporated within the mixed composition (typically present in either the oxidizing composition or the dye composition or both) in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Viscosity

The developer compositions and the dye compositions may be, independently from one another, prepared as so called thin liquids or creams.

Each of the non-diluted and diluted hair colouring compositions may have a viscosity which induces a shear stress of from 20 to 200 Pa at 10 $s^{-1}$ as measured according to the viscosity test method.

The non-diluted hair colouring composition may have a viscosity which induces a shear stress of from 20 to 200 Pa at 10 $s^{-1}$ as measured according to the viscosity test method and the diluted hair colouring composition may have a viscosity which induces a shear stress of from 20 to 180 Pa at 10 $s^{-1}$ as measured according to the viscosity test method.

Each of the non-diluted and diluted hair colouring compositions may have a viscosity which induces a shear stress of from 20 to 60 Pa at 10 $s^{-1}$, when the non-diluted and diluted hair colouring compositions are applied to the hair with a container to which a nozzle or a separate applicator device such as a comb or a brush is attached.

The non-diluted hair colouring composition may have a viscosity which induces a shear stress of from 30 to 200 Pa at 10 $s^{-1}$, or from 100 to 200 Pa at 10 $s^{-1}$ or from 130 to 180 Pa at 10 $s^{-1}$ when the non-diluted hair colouring composition is applied to the hair with a brush and bowl applicator. The diluted hair colouring composition may have a viscosity which induces a shear stress of from 20 to 180 Pa at 10 s$^{-1}$, or from 40 to 180 Pa at 10 s$^{-1}$, or from 70 to 170 Pa at 10 s$^{-1}$, when the non-diluted hair colouring composition is applied to the hair with a brush and bowl applicator or with the hands or fingers of the user.

Whilst not being bound by theory, it is believed that the provision of the non-diluted composition having viscosity values as described hereinabove enables the non-diluted composition to be applied directly to the roots without any dripping or running down the hair lengths and also enables the diluted composition to be easily applied and distributed along the entire remaining hair length with minimal to no dripping from the hair.

Application Means

Both the non-diluted and diluted hair colouring compositions may be applied to the hair with a brush and bowl applicator. Alternatively, the non-diluted hair colouring composition may be applied to the hair with a brush and bowl applicator whereas the diluted hair colouring composition may be applied to the hair with the hands and fingers of the user.

Alternatively, both the non-diluted and the diluted hair colouring compositions may be applied to the hair with a container to which a nozzle or a separate applicator device such as a comb is attached.

The application means may also include means which assist in achieving particular effects such as highlighting such as highlighting combs, brushes and tools, foils and highlighting caps. Additional application means technology can be used to assist in the penetration of the product into the hair. Examples of such technology include heating devices, ultraviolet light devices and ultrasound devices.

Hair Colouring Kit

The present invention also relates to a hair colouring kit which may be used for carrying out the method for colouring hair described hereinbefore. The compositions comprised in the kit may comprise any of the ingredients disclosed in the hair colouring compositions section of this application.

The kit may comprise a developer composition comprising one or more oxidizing agents, a dye composition comprising one or more oxidative dye precursor and/or one or more alkalizing agents and a dilutant composition comprising a non-aqueous liquid.

The developer composition may comprise from 1% to 20% by weight of the oxidizing agents and the dye composition may comprise from 0.01% to 10% by weight of the oxidative dye precursors and/or from 0.1% to 10% by weight of the alkalizing agents.

The kit may further comprise a shampoo for use in rinsing the hair after colouring and/or a conditioner composition.

The kit may also comprise a colour refresher composition. Such colour refresher composition may comprise at least one pre-formed dye and may be applied to the hair immediately after the oxidative colour. This is typically during the next wash cycle(s) from 1 day to 60 days after the original oxidative application. This colour refresher composition can be used to increase the initial colour obtained and/or boost the colour during the wash and style cycle until the next oxidative colouring or bleaching event.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The developer composition, the dye composition and the dilutant composition may be provided as separate containers in the kit. The developer composition container, the dye composition container and the dilutant composition container may be a bottle, a tube, an aerosol, or a sachet.

The developer composition may be provided as a container such as a bottle, a tube, an aerosol, or a sachet and the dye composition may be provided in an additional compartment within the developer container or in a separate container which may be identical such as a dual sachet or aerosol systems for example or different such as a bottle and tube system.

The consumer may mix the developer composition and the dye composition by any means. This may simply involve the use of a mixing bowl into which the compositions are dispensed and then mixed, preferably using a mixing means such as a tool. Alternatively, it may involve the addition of one of the compositions into the container of the other composition (typically the dye composition is added to the developer composition), followed by manual shaking or mixing with a tool. Another system involves the perforation or displacement of a seal located between the separate compartments of the dye composition and developer composition within a single container or sachet followed by manual mixing within the container or in a separate and/or additional container.

The hair colouring kit may further comprise an applicator. The applicator may be a brush and bowl applicator. Alternatively, the applicator may be a nozzle which may be attached to one of the containers comprised in the kit in case the developer composition, the dye composition and the dilutant composition are provided as separate containers in the kit or a separate applicator device such as a comb or a brush. Such combs and brushes can be adapted in order to achieve particular effects, whether it is quick and even coverage or root/hairline touch up, or highlights or streaks.

Alternatively, one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas.

The volume of developer composition in the kit may be 10 mL to 120 mL, or 40 mL to 70 mL, or 55 mL to 65 mL. The volume of dye composition in the kit may be 10 mL to 120 mL, or 40 mL to 70 mL, or 55 mL to 65 mL. The volume of dilutant composition may be 10 mL to 120 mL, or 15 mL to 30 mL, or 20 mL to 25 mL.

The compositions of the kit can be manufactured utilizing any one of the standard approaches, these include a) 'Oil in water' process, b) 'Phase Inversion' process and c) 'One-pot' process. For example, when using "oil in water" process, surfactants of the present invention are added to approximately 50% of total water amount of the compositions at about 90° C., homogenized for 15 to 30 min, then cooled to room temperature to form a premix; this premix is then mixed cold with remaining amounts of water, other optional components and/or oxidizing agent, thus forming the developer composition and dye composition of the above described colouring kit.

The kit may further comprise a set of instructions comprising instructing the user to colour its hair according to the method defined hereinbefore. The set of instruction may comprise:

i) mixing the developer composition with the dye composition to obtain a non-diluted hair colouring composition;
ii) applying a first portion of the non-diluted hair colouring composition obtained in step i) to the hair, preferably the hair roots and retaining a second portion of the non-diluted hair colouring composition obtained in step i);
iii) mixing the second portion with a dilutant composition comprising a non-aqueous liquid;
iv) applying a portion or all the diluted hair colouring composition to the hair, preferably the hair lengths and tips;
v) optionally rinsing the hair.

The set of instructions may comprise any additional step which is disclosed hereinbefore in the method for colouring hair section of the application.

Viscosity Test Method:

The viscosity of a composition is measured using a TA Instruments AR 2000 Rheometer or equivalent device equipped with a Peltier plate and a 6 cm flat acrylic plate with cross hatchings. The instrument is calibrated according to the manufacturer's instructions and the Peltier plate is set at 25.0° C. The cone is raised to a position approximately 4.5 cm above the plate.

Immediately after the mixing, approximately 10 g of the mixture is transferred gently onto the centre of the Peltier plate using a spatula. The cone is lowered to obtain the specified gap between the tip of the cone and the upper surface of the Peltier plate. The gap setting is specified by the manufacturer of the cone and is typically approximately 1000 microns. The rheometer is programmed to operate in rotational mode with the shear stress ramped from 0.1 to 600 Pa over a period of 4 minutes, termination at 1000 reciprocal seconds. Rotation is initiated immediately after the specified gap is established. Viscosity data collected during the measurement period are shear stress (Pa) plotted as a function of shear rate ($s^{-1}$).

Experimental Data:

All concentrations are listed as weight percent, unless otherwise specified.

Formulations Used to Generate the Experimental Data:

Dye composition formulation:

| Toluene-2.5-diamine sulfate | 0.16 |
| Resorcinol | 0.081 |
| 2-methylresorcinol | 0.005 |
| 2.4-diaminophenoxyethanol HCL | 0.005 |
| m-aminophenol | 0.003 |
| Ammonium hydroxide 25% | 4.137 |
| Hair colouring chassis | 95.609 |

Developer composition formulation:

| Water Purified | Up to 100 |
| Disodium EDTA. | 0.04 |
| Etidronic Acid | 0.08 |
| Aculyn 33 | 9.00 |
| Acrylates Steeareth-20 methacrylate copolymer | 0.05 |
| Hydrogen peroxide solution, 50% | 18.00 |
| Simethicone Emulsion | 0.01 |

In a first experiment, the dye composition was mixed with the developer composition at a mixing ratio of 1:1 in a bowl. 3 g of the resultant mixture was applied with a brush to a 0.75 g, 4 inch hair switch of uncoloured natural white hair and left for 30 minutes at 30° C. After 30 minutes the resultant mixture was rinsed off the hair for 2 minutes and the hair was then shampooed and conditioned for 1 minute and then blow-dried.

In a second experiment, the dye composition was mixed with the developer composition and glycerin at a mixing ratio of 1:1:1 in a bowl. 3 g of the resultant mixture was applied with a brush to a 0.75 g, 4 inch hair switch of uncoloured natural white hair and left for 30 minutes at 30° C. After 30 minutes the resultant mixture was rinsed off the hair for 2 minutes and the hair was then shampooed and conditioned for 1 minute and then blow-dried.

In both experiments, the hair was shampooed and conditioned in the same way and the colour of the hair was measured with an Ocean Optics USB 2000+ spectrophotometer. The measured L value (lightness value) is reported in the following table.

Results:

| Sample | L |
|---|---|
| dye composition + developer composition (Control) | 44.92 ± 1.31 |
| dye composition + developer composition + glycerin | 53.44 ± 1.41 |

As can be seen in the above table, the lightness value for the diluted hair colouring composition which is obtained by adding a dilutant composition comprising a non-aqueous liquid, namely glycerin to the non-diluted hair colouring composition, is higher than the lightness value for the non-diluted hair colouring composition. This demonstrates that by adding a non-aqueous dilutant composition to a hair colouring composition it is possible to reduce the dye deposition on hair resulting from the application of such a composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for colouring hair comprising the steps of:
   i) mixing a developer composition with a dye composition to obtain a non-diluted hair colouring composition, wherein the developer composition comprises one or more oxidizing agents and the dye composition comprises one or more oxidative dye precursors and/or one or more alkalising agents;
   ii) applying a first portion of the non-diluted hair colouring composition obtained in step i) to the hair, and retaining a second portion of the non-diluted hair colouring composition obtained in step i);
   iii) mixing the second portion with a dilutant composition comprising a non-aqueous liquid to obtain a diluted hair colouring composition;
   iv) applying a portion or all of the diluted hair colouring composition to the hair.

2. The method according to claim 1, wherein the first portion of the non-diluted hair colouring composition is applied to the hair roots and the portion or all of the diluted hair colouring composition is applied to the hair lengths and tips.

3. The method according to claim 1, wherein the method further comprises the step of:
   v) rinsing the hair.

4. The method according to claim 1, wherein the non-aqueous liquid is a water-miscible liquid or a water-immiscible liquid.

5. The method according to claim 4, wherein the water-miscible liquid is selected from the group consisting of alcohols, ethers, esters and mixtures thereof.

6. The method according to claim 4, wherein the water-immiscible liquid is an oil.

7. The method according to claim 6, wherein the oil is selected from the group consisting of fatty acids, lower alkanes, fatty alcohols, esters of fatty acid, esters of fatty alcohol, mineral oils, vegetable oils, animal oils, synthetic non-silicone oils, non-silicone waxes, silicones and mixtures thereof.

8. The method according to claim 1, wherein in step iii) the second portion of the non-diluted hair colouring composition obtained in step i) is mixed with the dilutant composition at a mixing ratio of about 30:1 or less.

9. The method according to claim 1, wherein in step ii) from about 90% to about 10% by weight of the non-diluted hair colouring composition obtained in step i) is applied as a first portion to the hair.

10. The method according to claim 1, wherein:
    a. the developer composition comprises from about 1% to about 20% by weight of the oxidizing agents and/or
    b. the dye composition comprises from about 0.01% to about 10% by weight of the oxidative dye precursors and/or from about 0.1% to about 10% by weight of the alkalising agents.

11. The method according to claim 1, wherein each of the non-diluted hair colouring composition and the diluted hair colouring composition has a viscosity which induces a shear stress of from about 20 to about 200 Pa at 10 s$^{-1}$ as measured according to the viscosity test method.

12. The method according to claim 1, wherein the non-diluted hair colouring composition has a viscosity which induces a shear stress of from about 20 to about 200 Pa at 10 s$^{-1}$ as measured according to the viscosity test method and the diluted hair colouring composition has a viscosity which induces a shear stress of from about 20 to about 180 Pa at 10 s$^{-1}$ as measured according to the viscosity test method.

13. The method according to claim 1, wherein the non-diluted hair colouring composition and the diluted hair colouring composition are applied to the hair with a brush and bowl applicator or a container to which a nozzle or a separate applicator device such as a comb or a brush is attached.

14. The method according to claim 1, wherein the non-diluted hair colouring composition and/or the diluted hair colouring composition comprise at least one gel network thickener system.

15. The method according to claim 1, wherein the developer composition comprises a thickener selected from acrylates copolymer, hydrophobically modified acrylate copolymers and mixtures thereof.

16. The method according to claim 3 wherein:
    a. the method further comprises the steps of waiting for a time period of from about 10 min to about 40 min which is performed between steps ii) and iv) and waiting for a time period of from about 5 min to about 20 min which is performed between steps iv) and v) or
    b. step iii) is performed immediately after step ii) and step iv) is performed immediately after step iii) and the method further comprises the step of waiting for a time period of from about 5 min to about 40 min which is performed between steps iv) and v).

17. A hair colouring kit comprising a developer composition comprising one or more oxidizing agents, a dye composition comprising one or more oxidative dye precursors and/or one or more alkalising agents and a dilutant composition comprising a non-aqueous liquid as defined in claim 1.

18. The hair colouring kit according to claim 17, wherein:
    a. the kit further comprises a brush and bowl applicator or
    b. the developer composition, the dye composition and the dilutant composition are provided as separate containers and the kit further comprises a nozzle.

* * * * *